(12) United States Patent
Li et al.

(10) Patent No.: US 9,448,188 B2
(45) Date of Patent: Sep. 20, 2016

(54) VEHICULAR RADIATION INSPECTION SYSTEM

(71) Applicants: Nuctech Company Limited, Haidian District, Beijing (CN); Tsinghua University, Haidian District, Beijing (CN)

(72) Inventors: Jianmin Li, Beijing (CN); Yinong Liu, Beijing (CN); Yulan Li, Beijing (CN); Chunguang Zong, Beijing (CN); Hui Gong, Beijing (CN); Qingping Huang, Beijing (CN); Weifeng Yu, Beijing (CN)

(73) Assignees: Nuctech Company Limited, Haidian District, Beijing (CN); Tsinghua University, Haidian District, Beijing (CN)

( * ) Notice: Subject to any disclaimer, the term of this patent is extended or adjusted under 35 U.S.C. 154(b) by 0 days.

(21) Appl. No.: 14/412,516

(22) PCT Filed: Jul. 2, 2013

(86) PCT No.: PCT/CN2013/078633
§ 371 (c)(1),
(2) Date: Jan. 2, 2015

(87) PCT Pub. No.: WO2014/005504
PCT Pub. Date: Jan. 9, 2014

(65) Prior Publication Data
US 2015/0192531 A1 Jul. 9, 2015

(30) Foreign Application Priority Data

Jul. 4, 2012 (CN) .......................... 2012 1 0231130

(51) Int. Cl.
*G01N 23/10* (2006.01)
*G01N 23/04* (2006.01)
*G01V 5/00* (2006.01)

(52) U.S. Cl.
CPC .............. *G01N 23/10* (2013.01); *G01N 23/04* (2013.01); *G01V 5/0016* (2013.01); *G01V 5/0066* (2013.01); *G01N 2223/301* (2013.01); *G01N 2223/308* (2013.01)

(58) Field of Classification Search
CPC ................. G01N 23/10; G01N 23/04; G01N 2223/301; G01N 2223/308; G01V 5/0066
See application file for complete search history.

(56) References Cited

U.S. PATENT DOCUMENTS

| | | | | |
|---|---|---|---|---|
| 5,838,759 | A * | 11/1998 | Armistead ............ | B66C 19/007 378/57 |
| 6,542,580 | B1 * | 4/2003 | Carver ................. | G01V 5/0008 378/57 |

(Continued)

FOREIGN PATENT DOCUMENTS

| CN | 1906479 A | 1/2007 |
|---|---|---|
| CN | 101027576 A | 8/2007 |

(Continued)

OTHER PUBLICATIONS

International Search Report for corresponding International Patent Application No. PCT/CN2013/078633 mailed Oct. 17, 2013 23552 Patent Trademark Office.

*Primary Examiner* — Christine Sung
(74) *Attorney, Agent, or Firm* — Merchant & Gould P.C.

(57) ABSTRACT

The present invention discloses a vehicular radiation inspection system comprising a mobile vehicle body, a detection arm, a radiation source and a detector. The vehicular radiation inspection system further comprises a following mechanism separated from the detection arm. The following mechanism contains radiation protection material, and the following mechanism follows the detection arm to move in a non-contact manner during inspection of the inspected object, so as to prevent radiation leakage. In the present invention, it does not need to infuse radiation protection material having a high density, such as lead, into the detection arm. Therefore, it can effectively decrease the weight of the detection arm, and it does not need to provide a balance counterweight on the mobile vehicle body on which the detection arm is carried, thereby effectively solving the problem that the vehicular radiation inspection system has an excessively large mass. Meanwhile, in the present invention, the moving process of the following mechanism is accurately controlled, so as to prevent the following mechanism from hitting the detection arm.

18 Claims, 3 Drawing Sheets

(56) References Cited

U.S. PATENT DOCUMENTS

| | | | |
|---|---|---|---|
| 7,453,987 B1 * | 11/2008 | Richardson | G01V 5/0041 378/57 |
| 7,483,510 B2 * | 1/2009 | Carver | G01N 23/04 378/197 |
| 7,663,109 B2 * | 2/2010 | Kang | G01V 5/0016 250/359.1 |
| 8,579,506 B2 * | 11/2013 | Morton | G01V 5/0008 378/194 |
| 2002/0136353 A1 * | 9/2002 | Kang | G01N 23/04 378/57 |
| 2004/0251415 A1 * | 12/2004 | Verbinski | G01N 23/02 250/358.1 |
| 2007/0217572 A1 | 9/2007 | Kotowski et al. | |
| 2008/0089476 A1 * | 4/2008 | Chen | G01V 5/0066 378/57 |
| 2008/0135772 A1 * | 6/2008 | Claus | G01V 5/0091 250/390.01 |

FOREIGN PATENT DOCUMENTS

| | | |
|---|---|---|
| CN | 101201326 A | 6/2008 |
| CN | 202256707 U | 5/2012 |
| CN | 202757896 U | 2/2013 |

* cited by examiner

VEHICULAR RADIATION INSPECTION SYSTEM

CROSS-REFERENCE TO RELATED APPLICATION

This application is a National Stage Application of PCT/CN2013/078633, filed Jul. 2, 2013, which claims the benefit of Chinese Patent Application No. 201210231130.7 filed on Jul. 4, 2012 in the State Intellectual Property Office of China, and which applications are incorporated herein by reference. To the extent appropriate, a claim of priority is made to each of the above disclosed applications.

BACKGROUND OF THE INVENTION

1. Field of the Invention

The present invention relates to a technical field of radiation inspection, more particularly, relates to a vehicular radiation inspection system.

2. Description of the Related Art

In the prior art, a vehicular container/vehicle inspection system is a kind of large container/vehicle inspection system, and can perform identifying organic/inorganic substance, quickly scanning and radioactivity monitoring. The core technology of the vehicular container/vehicle inspection system is a radiation imaging technology. A radiation source and a retractable detector arm are carried on a commercial vehicle chassis. During inspection, the detector arm is stretched out to form a scanning channel, and an inspected vehicle directly travels into the scanning channel and passes through the scanning channel. In the inspection, a radiation emitted from the radiation source mounted on the commercial vehicle passes through the inspected vehicle, and the detector arm receives the radiation to form a scanning image. Due to the need for radiation protection, a suitable amount of lead must be infused into the detector arm. This solution causes a problem that the detector arm has a large mass, significantly increasing a mass required for controlling the detector arm. In order to ensure the commercial vehicle chassis on which the detector arm is carried to be in balance, it is necessary to provide a balance counterweight on the commercial vehicle chassis. This will increase the mass and cost of the entire inspection system and decrease the flexibility of the entire inspection system. As a result, the vehicular container/vehicle inspection system cannot be rapidly transported. Concerning this, it is necessary to improve the vehicular container/vehicle inspection system of the prior art.

SUMMARY OF THE INVENTION

The present invention has been made to overcome or alleviate at least one aspect of the above mentioned disadvantages.

According to an aspect of the present invention, there is provided a vehicular radiation inspection system, comprising: a mobile vehicle body; a detection arm carried on the mobile vehicle body, a scanning channel being defined between the detection arm and the mobile vehicle body; a radiation source mounted on the mobile vehicle body and configured to emit a radiation onto an inspected object passing through the scanning channel; and a detector mounted on the detection arm and configured to receive the radiation emitted from the radiation source. The vehicular radiation inspection system further comprises a following mechanism separated from the detection arm, and the following mechanism contains radiation protection material, and the following mechanism follows the detection arm to move in a non-contact manner during inspection of the inspected object, so as to prevent radiation leakage.

According to a preferable embodiment of the present invention, lead for radiation protection is infused into the following mechanism, and the detection arm is not infused with lead for radiation protection.

According to another preferable embodiment of the present invention, the following mechanism has a receiving recess, and a part of the detection arm on which the detector is mounted is received in the receiving recess of the following mechanism during inspection of the inspected object.

According to another preferable embodiment of the present invention, there is a predetermined spacing distance between the following mechanism and the detection arm during inspection of the inspected object.

According to another preferable embodiment of the present invention, at least one sensor, for sensing an actual spacing distance between the following mechanism and the detection arm, is provided on the following mechanism.

According to another preferable embodiment of the present invention, a controller is provided on the following mechanism, and the controller calculates a target rotation speed of an electric motor for driving the following mechanism based on a distance difference between the predetermined spacing distance and the actual spacing distance sensed by the sensor, and controls the electric motor with the calculated target rotation speed, so as to keep the distance between the following mechanism and the detection arm equal to the predetermined spacing distance.

According to another preferable embodiment of the present invention, the controller calculates the target rotation speed of the electric motor based on the distance difference by means of a PID algorithm.

According to another preferable embodiment of the present invention, a frequency converter, for controlling the rotation speed of the electric motor, is provided on the following mechanism, and the target rotation speed is used as an instruction value for controlling the electric motor by the frequency converter.

According to another preferable embodiment of the present invention, an encoder, for detecting an actual rotation speed of the electric motor, is provided on the following mechanism, and the controller controls the rotation speed of the electric motor based on a rotation speed difference between the target rotation speed and the actual rotation speed detected by the encoder, so that the rotation speed of the electric motor is controlled to be equal to the target rotation speed.

According to another preferable embodiment of the present invention, the controller controls the rotation speed of the electric motor based on the rotation speed difference by means of a PID algorithm.

According to another preferable embodiment of the present invention, the controller is configured to be a programmable logic controller.

According to another preferable embodiment of the present invention, the following mechanism comprises a first sensor and a second sensor, and the first sensor and the second sensor are located at two sides of the detection arm respectively during inspection of the inspected object.

According to another preferable embodiment of the present invention, the sensor is configured to be a proximity switch.

According to another preferable embodiment of the present invention, the following mechanism comprises a pair of square pillar-like side wall portions facing to each other, and a plate-like bottom wall portion located between the pair of side wall portions.

According to another preferable embodiment of the present invention, the mobile vehicle body is not provided with a counterweight for balancing the weight of the detection arm.

According to another preferable embodiment of the present invention, the detection arm comprises a horizontal first arm connected to the mobile vehicle body, and a vertical second arm, on which the detector is mounted, connected to the horizontal first arm.

According to another preferable embodiment of the present invention, the detection arm is configured to be a retractable detection arm, and when it does not need to inspect the inspected object, the retractable detection arm is folded on the mobile vehicle body to facilitate transportation, and when it needs to inspect the inspected object, the retractable detection arm is stretched out to form the scanning channel.

According to another preferable embodiment of the present invention, the following mechanism is configured to be capable of being carried on and transported with the mobile vehicle body when it does not need to inspect the inspected object.

According to another preferable embodiment of the present invention, the following mechanism and the mobile vehicle body are configured to be a rail type of following mechanism and a rail type of mobile vehicle body, respectively, which can move on rails parallel to each other.

According to another preferable embodiment of the present invention, the following mechanism and the mobile vehicle body are configured to be a non-rail type of following mechanism and a non-rail type of mobile vehicle body, respectively, which move only by wheels.

Compared with the prior art, the present invention is advantageous at least in that since an independent following mechanism separated from the detection arm and having a radiation protection function is provided, it does not need to infuse radiation protection material with high density, such as lead, into the detection arm. Therefore, the weight of the detection arm can be effectively decreased, and no balance counterweight is needed to be provided on the mobile vehicle body on which the detection arm is carried, thereby effectively solving the problem that the vehicular radiation inspection system has an excessive large mass, and thereby effectively providing radiation protection to ensure the safety. Meanwhile, in the present invention, the moving process of the following mechanism is accurately controlled, so as to prevent collision between the following mechanism and the detection arm.

DETAILED DESCRIPTION OF PREFERRED EMBODIMENTS OF THE INVENTION

Figure 1A:
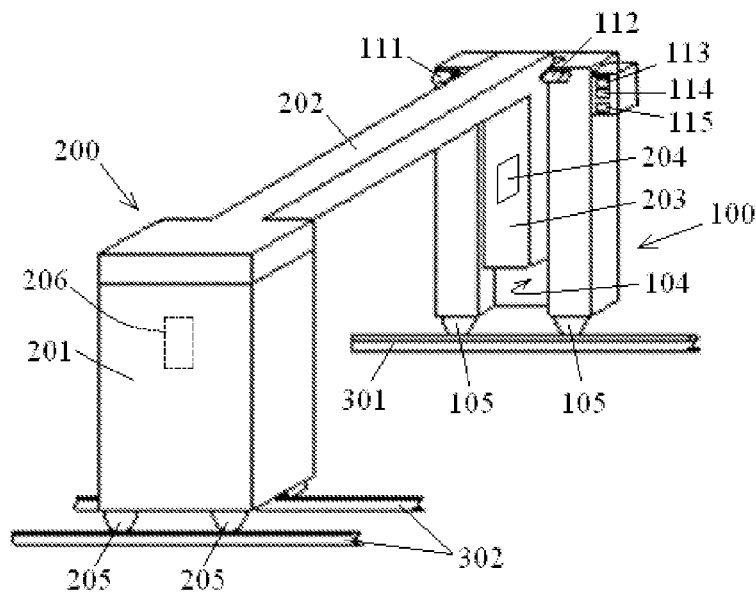
FIG. 1a is an illustrative perspective view of a vehicular radiation inspection system according to an embodiment of the present invention.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

Figure 1B:
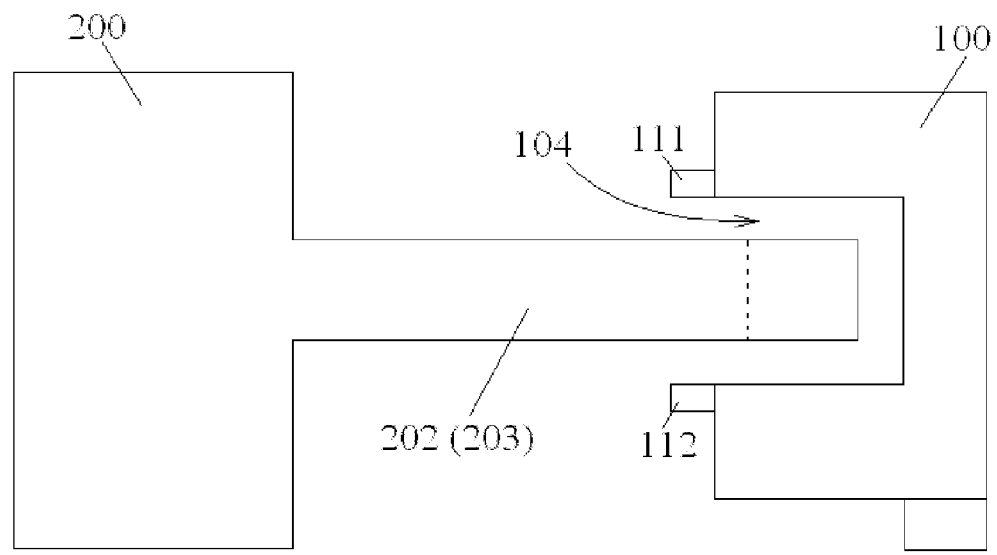
FIG. 1b is a top view of the vehicular radiation inspection system of FIG. 1a, wherein a following mechanism, following a detection arm in a non-contact manner, is shown.
Figure 2:
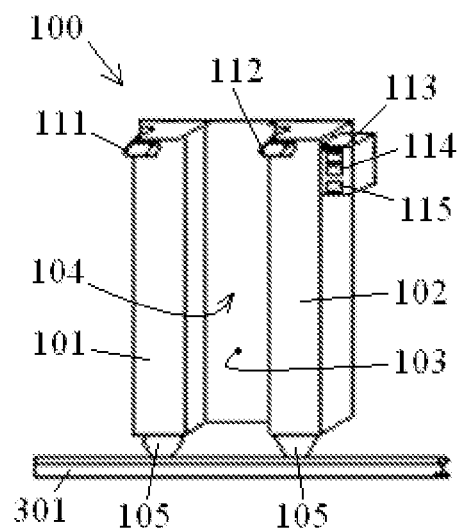
FIG. 2 is an illustrative perspective view of the following mechanism of FIG. 1.
Figure 3:
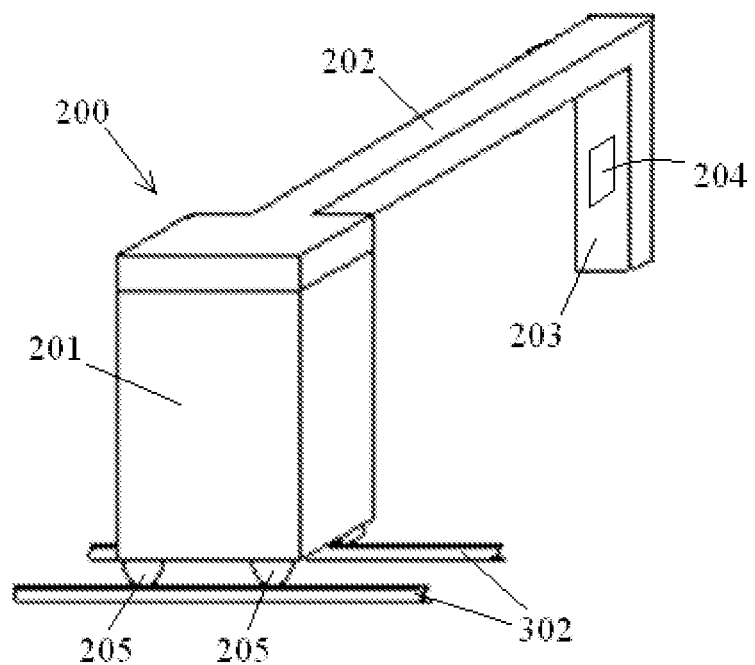
FIG. 3 is an illustrative perspective view of a mobile vehicle body with the detection arm of FIG. 1.

FIG. 1a is an illustrative perspective view of a vehicular radiation inspection system according to an embodiment of the present invention. FIG. 1b is a top view of the vehicular radiation inspection system of FIG. 1a, wherein a following mechanism, following a detection arm in a non-contact manner, is shown. FIG. 2 is an illustrative perspective view of the following mechanism of FIGS. 1a and 1b. FIG. 3 is an illustrative perspective view of a mobile vehicle body with the detection arm of FIGS. 1a and 1b.

As shown in FIGS. 1a, 1b, 2 and 3, in an embodiment of the present invention, the vehicular radiation inspection system mainly comprises an inspection vehicle 200 and a following mechanism 100 separated from the inspection vehicle 200.

As shown in FIG. 3, the inspection vehicle 200 mainly comprises a mobile vehicle body 201 and a detection arm 202, 203 carried on the mobile vehicle body 201.

As shown in FIGS. 1a, 1b and 3, a scanning channel, for allowing an inspected object (not shown, for example, a container or a vehicle) to pass therethrough, is defined between the detection arm 202, 203 and the mobile vehicle body 201.

As shown in FIGS. 1a and 1b, a radiation source 206 is mounted on the mobile vehicle body 201 and configured to emit a radiation onto the inspected object passing through the scanning channel.

As shown in FIGS. 1a, 1b and 3, a detector 204, corresponding to the radiation source, is mounted on the detection arm and configured to receive the radiation emitted from the radiation source and passing through the inspected object.

In the illustrated embodiment, the detection arm 202, 203 mainly comprises a horizontal first arm 202 and a vertical second arm 203. As shown in FIGS. 1a, 1b and 3, the horizontal first arm 202 is connected to the mobile vehicle body 201, and the vertical second arm 203 is connected to the horizontal first arm 202. The detector 204 is mounted on the vertical second arm 203.

Although not shown, in an embodiment of the present invention, the horizontal first arm 202 may be rotatable in one or more directions relative to the mobile vehicle body 201. Also, the vertical second arm 203 may be rotatable in one or more directions relative to the horizontal first arm 202. In this way, the first and second detection arms 202, 203 constitute a retractable and folding detection arm. When it does not need to inspect the inspected object, the first and second detection arms 202, 203 are folded on the mobile vehicle body 201 for transportation. When it needs to inspect the inspected object, the first and second detection arms 202, 203 are stretched out to form the scanning channel.

As shown in FIGS. 1a, 1b and 2, the vehicular radiation inspection system further comprises a following mechanism 100 separated from the detection arm 202, 203. The following mechanism 100 comprises a pair of square pillar-like side wall portions 101, 102 facing to each other, and a plate-like bottom wall portion 103 located between the pair of side wall portions 101, 102. The pair of side wall portions 101, 102 and the plate-like bottom wall portion 103 together define a receiving recess 104. The second detection arm 203 is received in the receiving recess 104.

It should be noted that the mechanical structure of the following mechanism 100 is not limited to the illustrated embodiments, and the following mechanism may have other structures as long as the following mechanism has a receiving recess 104 adapted to receive the second detection arm 203 therein.

In the present invention, the following mechanism 100 contains radiation protection material, for example, lead. In a preferable embodiment of the present invention, lead for radiation protection is infused into the following mechanism 100.

As shown in FIGS. 1a and 1b, during inspection of the inspected object, the second detection arm 203 of the detection arm 202, 203 on which the detector 204 is mounted is received in the receiving recess 104 of the following mechanism 100, so as to prevent radiation leakage.

Since the detector 204 is mounted on the second detection arm 203, the ray emitted from the radiation source will irradiate the second detection arm 203. In the present invention, the second detection arm 203 is received in the receiving recess 104 having a radiation protection function. In this way, the ray irradiated on the second detection arm 203 can be prevented from leakage, thereby achieving a good radiation protection and protecting the surrounding environment and the operator from the ray.

Meanwhile, since the following mechanism 100 is an independent mechanism separated from the detection arm 203, it does not need to infuse radiation protection material have a high density into the detection arm 203, so that the weight of the detection arm 203 can be significantly decreased. Therefore, there is no need to provide a balance counterweight on the mobile vehicle body 201 on which the detection arm 203 is carried, thereby effectively solving the problem that the vehicular radiation inspection system has an excessively large mass and providing an effective radiation protection to ensure the safety.

As shown in FIGS. 1a and 1b, during inspection of the inspected object, the following mechanism 100 follows the detection arms 202, 203 to move.

In a preferable embodiment of the present invention, in order to prevent the following mechanism 100 from hitting the detection arms 202, 203 during inspection of the inspected object, the following mechanism 100 is controlled to follow the detection arms 202, 203 in a non-contact manner all the time during inspection of the inspected object.

Figure 4:
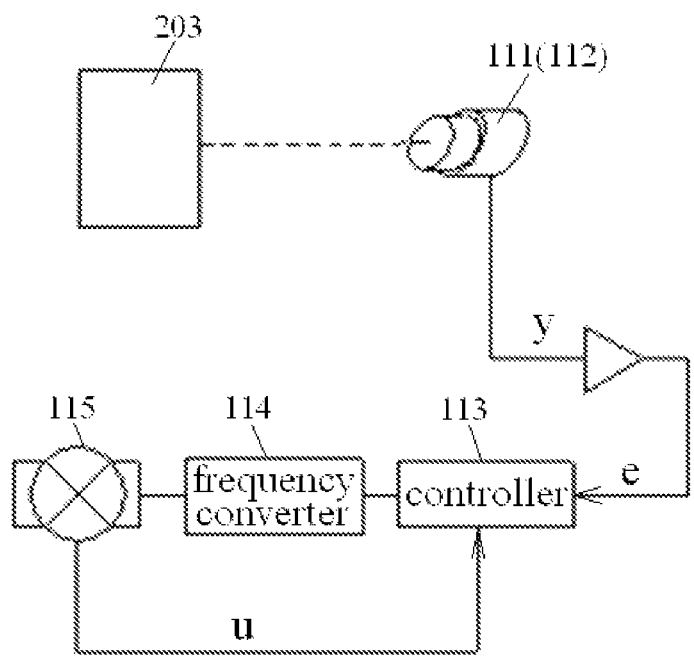
FIG. 4 shows a control process of the vehicular radiation inspection system of FIG. 1.

FIG. 4 shows a control process of the vehicular radiation inspection system of FIGS. 1a and 1b.

As shown in FIGS. 1a, 1b, 2 and 4, in order to control the following mechanism 100 as described above, at least one sensor 111, 112 is provided on the following mechanism 100. The at least one sensor 111, 112 is used to sense an actual spacing distance y between the following mechanism 100 and the detection arms 202, 203.

In a preferable embodiment of the present invention, a pair of sensors 111, 112, comprising a first sensor 111 and a second sensor 112, are provided on the following mechanism 100. As shown in FIGS. 1a and 1b, the first sensor 111 and the second sensor 112 are located at two sides of the detection arm 202, 203, respectively, during inspection of the inspected object.

However, it should be noted that the present invention is not limited to the illustrated embodiments, and the following mechanism 100 may be provided with only a single sensor. An object of providing a plurality of sensors is to increase the reliability of the system, for example, when one of the sensors is failed, the other sensors can normally work. In this way, it can reliably prevent the following mechanism from hitting the detection arms 202, 203.

Figure 5:
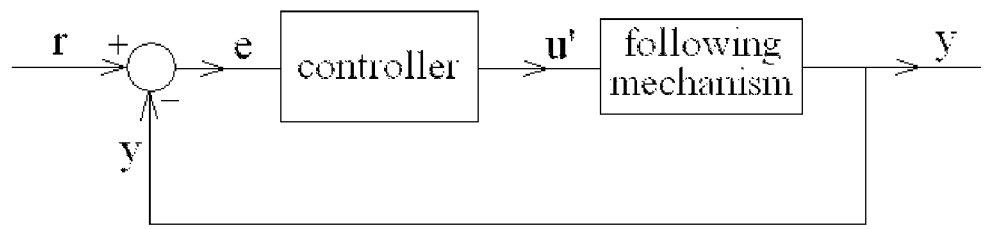
FIG. 5 shows a control block diagram of controlling a distance between the following mechanism and the detection arm in the vehicular radiation inspection system of FIG. 1.

FIG. 5 shows a control block diagram of controlling a distance between the following mechanism and the detection arm in the vehicular radiation inspection system of FIGS. 1a and 1b.

As shown in FIGS. 4 and 5, in a preferable embodiment of the present invention, during inspection of the inspected object, the following mechanism 100 is controlled to keep a predetermined spacing distance r from the detection arms 202, 203 constant.

As shown in FIGS. 1a, 1b, 2 and 4, a controller 113 is provided on the following mechanism 100, and the controller 113 calculates a target rotation speed u' of an electric motor for driving the following mechanism 100 based on a distance difference e between the predetermined spacing distance r and the actual spacing distance y sensed by the sensors 111, 112, and controls the electric motor with the calculated target rotation speed u', so as to keep the distance between the following mechanism 100 and the detection arm 202, 203 equal to the predetermined spacing distance r.

In a preferable embodiment of the present invention, the controller 113 calculates the target rotation speed u' of the electric motor based on the distance difference e by means of a PID (Proportion Integration Differentiation) algorithm. But the present invention is not limited to this, and the controller 113 may adopt any other suitable control algorithms to control the spacing distance between the following mechanism 100 and the detection arms 202, 203.

Since the PID algorithm is a typical control algorithm, for the purpose of conciseness, its description in detail is omitted herein.

As shown in FIGS. 1a, 1b, 2 and 4, a frequency converter 114, for controlling the rotation speed of the electric motor, is provided on the following mechanism 100. The target rotation speed u' from the controller 113 is used as an instruction value for the frequency converter 114 controlling the electric motor.

Figure 6:
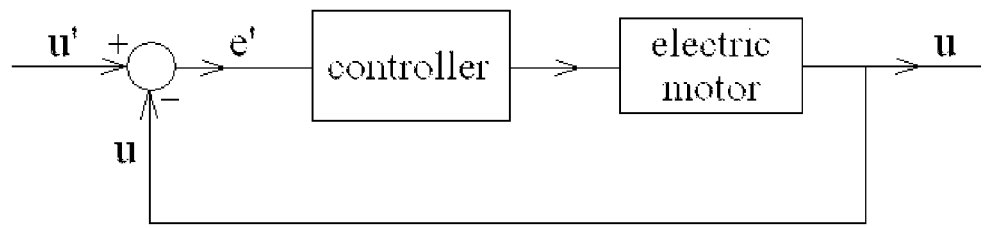
FIG. 6 shows a control block diagram of controlling a rotation speed of a driving electric motor for the following mechanism in the vehicular radiation inspection system of FIG. 1.

FIG. 6 shows a control block diagram of controlling a rotation speed of a driving electric motor of the following mechanism in the vehicular radiation inspection system of FIGS. 1a and 1b.

In order to control the rotation speed of the electric motor for driving the following mechanism 100 to reach a target rotation speed u', as shown in FIGS. 1a, 2 and 4, an encoder 115, for detecting an actual rotation speed u of the electric motor, is provided on the following mechanism 100.

As shown in FIG. 6, in a preferable embodiment of the present invention, the controller 113 controls the rotation speed of the electric motor based on a rotation speed difference e' between the target rotation speed u' and the actual rotation speed u detected by the encoder 115, so that the rotation speed of the electric motor is controlled to be equal to the target rotation speed u'.

In a preferable embodiment of the present invention, the controller 113 controls the rotation speed of the electric motor based on the rotation speed difference e' by means of a PID algorithm.

In an embodiment of the present invention, the controller may be a programmable logic controller, a single chip microcomputer or a personal computer.

In an embodiment of the present invention, the sensor 111, 112 is configured to be a proximity switch. Of course, the sensor may be any other suitable distance sensors, for example, an acoustic distance sensor, an optical distance sensor, a contact distance sensor and so on.

As shown in FIGS. 1a, 1b, 2 and 3, the following mechanism 100 and the mobile vehicle body 201 may be configured to be a rail type of following mechanism and a rail type of mobile vehicle body, respectively, moving on rails 301, 302 parallel to each other by means of wheels 105, 205.

However, the present invention is not limited to this, and the following mechanism 100 and the mobile vehicle body 201 may be configured to be a non-rail type of following mechanism and a non-rail type of mobile vehicle body, respectively, moving along a predetermined parallel path by wheels 105, 205.

In the present invention, when it does not need to inspect the inspected object, the following mechanism 100 is carried on the mobile vehicle body 201 and be transported with the mobile vehicle body 201.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

What is claimed is:

1. A vehicular radiation inspection system, comprising:
   a mobile vehicle body;
   a detection arm carried on the mobile vehicle body and defining a scanning channel together with the mobile vehicle body;
   a radiation source mounted on the mobile vehicle body and configured to emit a ray onto an inspected object passing through the scanning channel; and
   a detector mounted on the detection arm and configured to receive the ray emitted from the radiation source,
   wherein the vehicular radiation inspection system further comprising a following mechanism separate from the detection arm,
   wherein the following mechanism contains radiation protection material, and the following mechanism follows the detection arm to move in a non-contact manner during inspecting the inspected object, so as to prevent radiation leakage,
   wherein at least one sensor, for sensing an actual gap distance between the following mechanism and the detection arm, is provided on the following mechanism,
   wherein there is a predetermined gap distance between the following mechanism and the detection arm during inspecting the inspected object.

2. The vehicular radiation inspection system according to claim 1,
   wherein lead for radiation protection is infused into the following mechanism, and the detection arm is not infused with lead for radiation protection.

3. The vehicular radiation inspection system according to claim 1,
   wherein the following mechanism has a receiving recess, and a part of the detection arm, on which the detector is mounted, is received in the receiving recess of the following mechanism during inspecting the inspected object.

4. The vehicular radiation inspection system according to claim 1, wherein a controller is provided on the following mechanism, and the controller calculates a target rotation speed of an electric motor for driving the following mechanism based on a distance difference between the predetermined gap distance and the actual gap distance sensed by the sensor, and controls the electric motor with the calculated target rotation speed, so as to keep the distance between the following mechanism and the detection arm equal to the predetermined gap distance.

5. The vehicular radiation inspection system according to claim 4,
   wherein the controller calculates the target rotation speed of the electric motor based on the distance difference by means of a PID algorithm.

6. The vehicular radiation inspection system according to claim 5,
   wherein a frequency converter, for controlling the rotation speed of the electric motor, is provided on the following mechanism, and
   wherein the target rotation speed is used as an instruction value of the frequency converter to control the electric motor.

7. The vehicular radiation inspection system according to claim 6,
   wherein an encoder, for detecting an actual rotation speed of the electric motor, is provided on the following mechanism, and
   wherein the controller controls the rotation speed of the electric motor based on a rotation speed difference between the target rotation speed and the actual rotation speed detected by the encoder, so that the rotation speed of the electric motor is controlled to be equal to the target rotation speed.

8. The vehicular radiation inspection system according to claim 7,
   wherein the controller controls the rotation speed of the electric motor based on the rotation speed difference by means of a PID algorithm.

9. The vehicular radiation inspection system according to claim 4,
   wherein the controller is configured to be a programmable logic controller.

10. The vehicular radiation inspection system according to claim 1,
    wherein the at least one sensor on the following mechanism comprises a first sensor and a second sensor, and
    wherein the first sensor and the second sensor are located at both sides of the detection arm, respectively.

11. The vehicular radiation inspection system according to claim 10, wherein at least one of the first and second sensors is configured to be a proximity switch.

12. The vehicular radiation inspection system according to claim 1, wherein the following mechanism comprising:
    a pair of pillar-like side wall portions facing to each other; and
    a plate-like bottom wall portion located between the pair of side wall portions.

13. The vehicular radiation inspection system according to claim 1, wherein the mobile vehicle body is not provided with a counterweight for balancing the weight of the detection arm.

14. The vehicular radiation inspection system according to claim 1, wherein the detection arm comprising:
   a horizontal first arm connected to the mobile vehicle body; and
   a vertical second arm, on which the detector is mounted, connected to the horizontal first arm.

15. The vehicular radiation inspection system according to claim 1,
   wherein the detection arm is configured to be a retractable detection arm,
   when it does not need to inspect the inspected object, the retractable detection arm is folded on the mobile vehicle body to facilitate shipping, and
   when it needs to inspect the inspected object, the retractable detection arm is stretched out to form the scanning channel.

16. The vehicular radiation inspection system according to claim 1,
   wherein the following mechanism is configured to be capable of being carried on and shipped with the mobile vehicle body when it does not need to inspect the inspected object.

17. The vehicular radiation inspection system according to claim 1,
   wherein the following mechanism and the mobile vehicle body are configured to a rail type of following mechanism and a rail type of mobile vehicle body, respectively, moving on rails parallel to each other.

18. The vehicular radiation inspection system according to claim 1,
   wherein the following mechanism and the mobile vehicle body are configured to a railless following mechanism and a railless mobile vehicle body, respectively, moving only by wheels.

* * * * *